United States Patent
Kobayashi et al.

(10) Patent No.: US 9,351,636 B2
(45) Date of Patent: May 31, 2016

(54) SUBJECTIVE EYE REFRACTING POWER MEASUREMENT APPARATUS

(71) Applicant: NIDEK CO., LTD., Gamagori, Aichi (JP)

(72) Inventors: Toshihiro Kobayashi, Aichi (JP); Yoshinobu Hosoi, Aichi (JP)

(73) Assignee: NIDEK CO., LTD., Aichi (JP)

(*) Notice: Subject to any disclaimer, the term of this patent is extended or adjusted under 35 U.S.C. 154(b) by 69 days.

(21) Appl. No.: 14/167,368

(22) Filed: Jan. 29, 2014

(65) Prior Publication Data

US 2014/0211165 A1 Jul. 31, 2014

(30) Foreign Application Priority Data

Jan. 30, 2013 (JP) .................................. 2013-016259
Jan. 30, 2013 (JP) .................................. 2013-016260

(51) Int. Cl.
*A61B 3/02* (2006.01)
*A61B 3/032* (2006.01)

(52) U.S. Cl.
CPC ...................................... *A61B 3/032* (2013.01)

(58) Field of Classification Search
CPC ............ A61B 3/14; A61B 3/103; A61B 3/12; A61B 3/02
USPC ......................................... 351/222, 237, 238
See application file for complete search history.

(56) References Cited

U.S. PATENT DOCUMENTS

| 2002/0018179 A1* | 2/2002 | Hayashi et al. | 351/204 |
|---|---|---|---|
| 2002/0026179 A1* | 2/2002 | Toh | 606/5 |
| 2005/0018132 A1* | 1/2005 | Fukuma et al. | 351/200 |
| 2011/0032479 A1* | 2/2011 | Utsunomiya | 351/206 |

FOREIGN PATENT DOCUMENTS

| JP | 59-085642 A | 5/1984 |
|---|---|---|
| JP | 05-176893 A | 7/1993 |

* cited by examiner

*Primary Examiner* — Mahidere Sahle
(74) *Attorney, Agent, or Firm* — Sughrue Mion, PLLC

(57) ABSTRACT

There is provided a subjective eye refracting power measurement apparatus which measures a refracting power of a subject eye. The apparatus includes a projection optical system which projects a visual target light flux toward the subject eye to form a visual target on a fundus of the subject eye; a correction optical system which changes a refracting power thereof; a relay optical system which relays a light flux passing through the correction optical system and to form an image of the correction optical system in front of the subject eye; a deviation detector which detects a positional deviation of the image of the correction optical system with respect to the subject eye; and a correction unit which optically corrects a formation position of the image based on a detection result by the deviation detector such that the image is formed in front of the subject eye.

20 Claims, 11 Drawing Sheets

SUBJECTIVE EYE REFRACTING POWER MEASUREMENT APPARATUS

CROSS-REFERENCE TO RELATED APPLICATION

This application claims priority from Japanese Patent Application Nos. 2013-016259 and 2013-016260, both filed on Jan. 30, 2013, the entire subject matter of which is incorporated herein by reference.

TECHNICAL FIELD

The present disclosure relates to a subjective eye refracting power measurement apparatus which presents a visual target to a subject eye.

BACKGROUND

There has been known a subjective eye refracting power measurement apparatus which individually disposes a refractive power adjustable correction optical system in front of a subject eye, and projects an eye-examination visual target on a fundus of the subject eye via the correction optical system (refer to JP-A-H5-176893). While receiving a response from a subject person, an examiner adjusts the correction optical system until the subject person can properly see the visual target to obtain a correction value, and measures a refracting power of the subject eye based on the correction value.

Further, there has been also known an apparatus which is configured not to dispose such correction optical system in front of the subject eye, but to be able to form an image of the correction optical system in front of the subject eye via a relay optical system (refer to JP-A-S59-85642).

JP-A-S59-85642 discloses a configuration in which a presentation distance of the visual target can be switched to a distance for a near distance examination. However, in JP-A-S59-85642, a presentation direction of the visual target is not changed between the far distance examination and the near distance examination.

SUMMARY

Accordingly, an aspect of the present disclosure provides a subjective eye refracting power measurement apparatus which can smoothly measure an eye refracting power without disposing a correction optical system in front of a subject eye.

According to an illustrative embodiment of the present disclosure, there is provided a subjective eye refracting power measurement apparatus configured to measure a refracting power of a subject eye, the apparatus comprising: a projection optical system configured to project a visual target light flux toward the subject eye to form an eye-examination visual target on a fundus of the subject eye; a correction optical system disposed in an optical path of the projection optical system and configured to change a refracting power thereof; a relay optical system configured to relay a light flux passing through the correction optical system and to form an image of the correction optical system in front of the subject eye; a deviation detector configured to detect a positional deviation of the image of the correction optical system with respect to the subject eye; and a correction unit configured to optically correct a formation position of the image of the correction optical system based on a detection result by the deviation detector such that the image of the correction optical system is formed in front of the subject eye.

According to another illustrative embodiment of the present disclosure, there is provided a subjective eye refracting power measurement apparatus configured to measure a refracting power of a subject eye, the apparatus comprising: a projection optical system configured to project a visual target light flux toward the subject eye to form an eye-examination visual target on a fundus of the subject eye; a correction optical system disposed in an optical path of the projection optical system and configured to change a refracting power thereof; a relay optical system configured to relay a light flux passing through the correction optical system and to form an image of the correction optical system in front of the subject eye; a distance change unit configured to optically change a presentation distance of the visual target between for a far distance examination and for a near distance examination; and an optical path switch unit configured to switch between a first optical path for projecting the visual target light flux toward the subject eye from a horizontal direction and a second optical path for projecting the visual target light flux toward the subject eye from a direction which is tilted downward with respect to the horizontal direction.

According to this configuration, the visual target is properly presented to the subject person.

BRIEF DESCRIPTION OF THE DRAWINGS

The above and other aspects of the present disclosure will become more apparent and more readily appreciated from the following description of illustrative embodiments of the present disclosure taken in conjunction with the attached drawings, in which.

DESCRIPTION OF ILLUSTRATIVE EMBODIMENTS

First Illustrative Embodiment

Figure 1A:
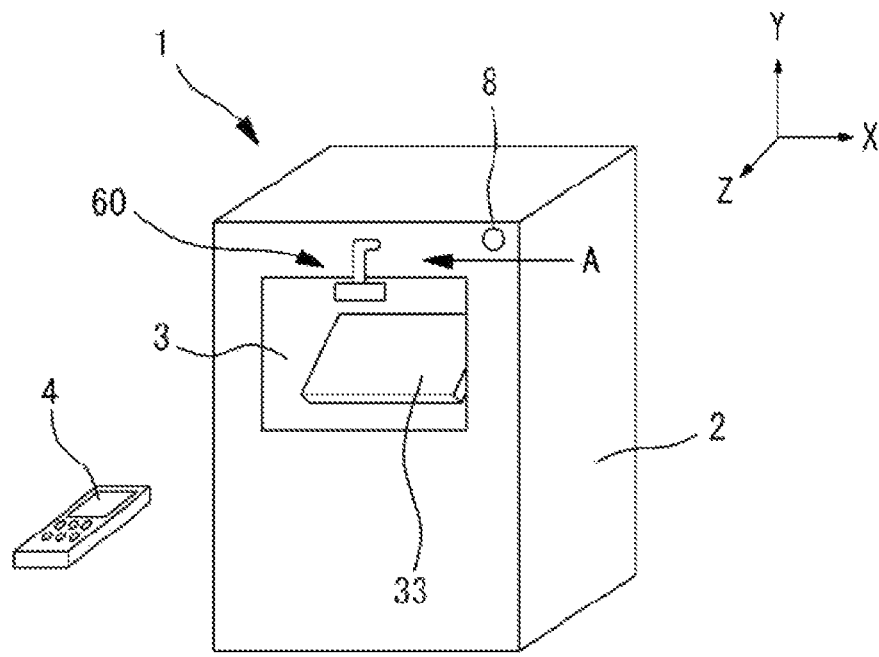
FIGS. 1A and 1B are outer configuration views of a subjective eye refracting power measurement apparatus according to an illustrative embodiment.
Figure 1B:
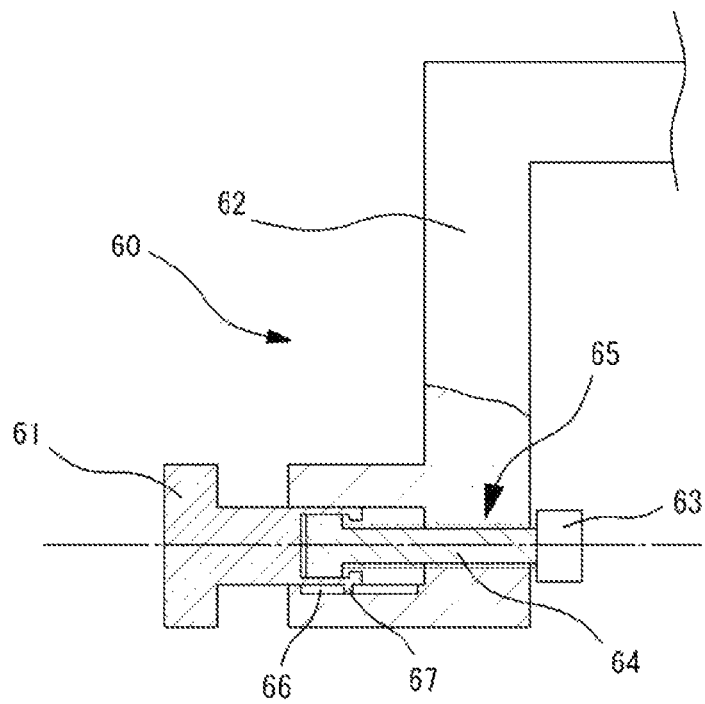
Figure 2:
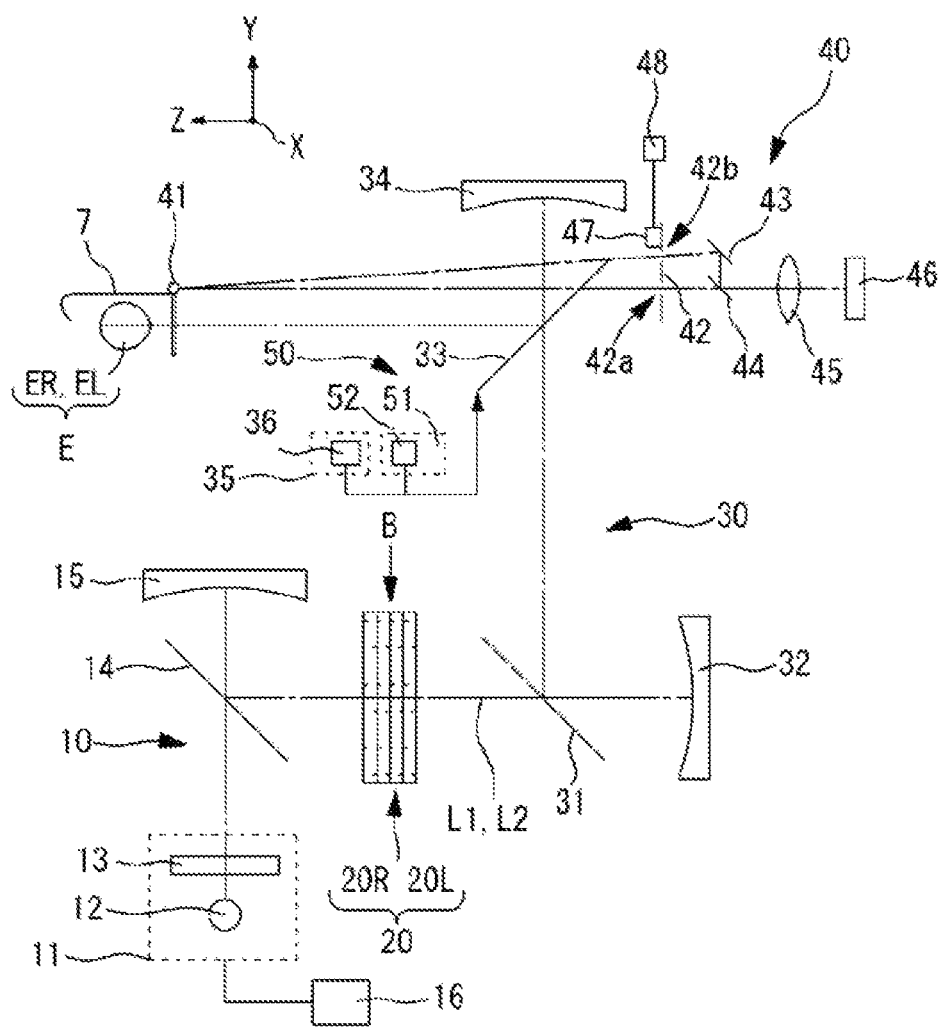
FIG. 2 is a schematic view of an optical system of the subjective eye refracting power measurement apparatus according to the illustrative embodiment.

FIGS. 1A and 1B are outer configuration views of a subjective eye refracting power measurement apparatus according to a first illustrative embodiment. FIG. 2 is a schematic view showing an internal configuration of the apparatus according to the first illustrative embodiment. The apparatus according to this illustrative embodiment mainly includes: a visual target projection system 10; a correction optical system 20; a relay optical system 30; a detection optical system 40; and a deviation correction unit 50. The visual target projection system 10 is a projection optical system which projects a visual target toward a subject eye E. The correction optical system 20 is configured to change a refraction degree of each of eye-examination visual target light fluxes which are directed toward the left and right eyes E of the subject person. The relay optical system 30 relays the visual target passing through the correction optical system 20 to the subject eye E. The detection optical system 40 is a deviation detector which detects a positional deviation of the subject eye E. The detection optical system 40 detects a positional deviation of the subject eye E during an eye refracting power measurement. The deviation correction unit 50 corrects an image formation position of the eye-examination visual target, based on the positional deviation of the eye. Hereinafter, R and L affixed to reference signs indicate the right eye and the left eye, respectively. In the following description, with regard to a positional relationship between the subject eye E and the apparatus, a front and rear direction, a left and right direction, and an upper and lower direction indicate, respectively, a Z direction, an X direction, and a Y direction in a state where the subject eye E and the apparatus face each other.

<Outer Configuration>

FIG. 1A is a schematic perspective view of the subjective eye refracting power measurement apparatus 1 (hereinafter, referred to as an apparatus) according to the illustrative embodiment. The apparatus 1 includes a housing 2; a presentation window 3 for presenting the visual target (optotype) to a subject person; a controller 4 which operates the apparatus 1; a forehead rest 60 which maintains a constant distance between the subject eye E and the apparatus 1; and the like.

FIG. 1B is a view of the forehead rest 60 according to the illustrative embodiment when seen from the A direction shown in FIG. 1A. The forehead rest 60 includes a contact portion 61, a connection portion 62, a rotational knob 63, and a feed screw 64. The feed screw 64 is screwed into a female screw 65 of the connection portion 62. The feed screw 64 is engaged with the contact portion 61. The rotational knob 63 is provided in an end portion of the feed screw 64 on a side of the apparatus 1. The connection portion 62 is formed with a groove 66. The contact portion 61 has a convex portion 67. The groove 66 and the convex portion 67 prevent the contact portion 61 from rotating.

That is, when an examiner rotates the rotational knob 63, the contact portion 61 protrudes or retracts in a direction of a rotation axis of the feed screw 64. Accordingly, the contact portion 61 is movable in the Z direction by an operation of the rotational knob 63.

The apparatus 1 of the illustrative embodiment includes a notification unit 8. The notification unit 8 notifies whether the apparatus 1 and the subject eye E are appropriately positioned in the Z direction. A light source, a speaker, or the like is used as the notification unit 8. The notification unit 8 will be described in detail.

The visual target projection system 10, the correction optical system 20, the relay optical system 30, the detection optical system 40, the deviation correction unit 50, and the like are disposed in the housing 2.

<Visual Target Projection System>

The visual target projection system 10 will be described with reference to FIG. 2. The visual target projection system 10 includes, for example, a visual target projection unit 11, a half mirror 14, a concave mirror 15, a drive unit 16, and the like. The visual target projection unit 11 includes, for example, a light source 12, a liquid crystal display 13, and the like, and projects the eye-examination visual target.

The liquid crystal display 13 has, for example, a structure in which special liquid is sealed between two glass plates, a voltage is applied to change orientations of liquid crystal molecules such that a light transmittance is increased or decreased, and thus, an image is displayed. The liquid crystal display 13 passes light emitted from the light source 12 such that the displayed image is projected.

The visual target projection unit 11 can project various eye-examination visual targets to detect a spherical power, a cylindrical power, a cylindrical axis, and the like. For example, a display of the display 13 is controlled by a control unit 90, and thus, the eye-examination visual target is selected and is projected by the light source 12.

A light flux of the projected eye-examination visual target of the display 13 is transmitted through the half mirror 14, and is reflected by the concave mirror 15. The reflected light flux is reflected by the half mirror 14. The reflected light flux is incident on a pair of correction optical systems 20R and 20L.

The drive unit 16 can move the visual target projection unit 11 toward or away from the concave mirror 15. The drive unit 16 operates as a distance change unit which optically changes a presentation distance of the visual target between for a far distance examination and for a near distance examination.

<Correction Optical System>

Figure 3:
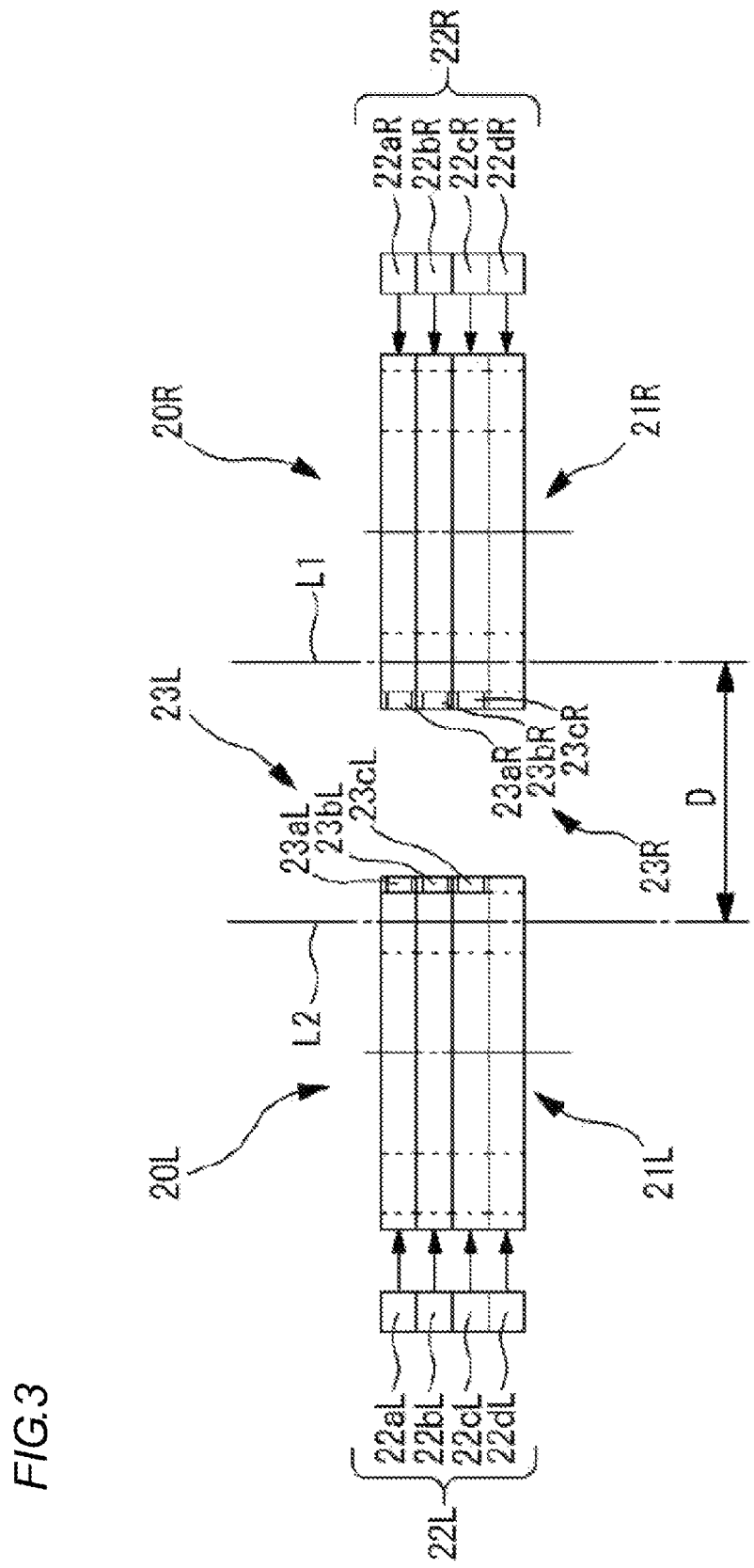
FIG. 3 is a schematic view of a correction optical system according to the illustrative embodiment.

Each of the correction optical systems 20R and 20L corrects a spherical power, a cylindrical power, a cylindrical axis, and the like. The correction optical system 20R is for a right eye measurement, and the correction optical system 20L is for a left eye measurement. Those correction optical systems 20R and 20L have the same optical configuration. FIG. 3 is a schematic view of the correction optical systems 20R and 20L when seen from the B direction shown in FIG. 2.

As shown in FIG. 3, if eye-examination optical paths of the correction optical systems 20R and 20L are defined as an optical path L1 and an optical path L2, respectively, a distance D between the optical paths L1 and L2 is set to be an inter-pupil distance of the subject person.

The correction optical systems 20R and 20L will be described by taking the correction optical system 20R as an example. In a lens disc 21R provided in the correction optical system 20R, many optical elements (a spherical lens, a cylindrical lens, a dispersion prism, and the like) are disposed at the same circle. When a drive unit (an actuator or the like) 22R controls the lens disc 21R to rotate, an optical element desired by the examiner is disposed in the optical path L1 for the right eye examination.

When a drive unit 23R controls the optical element (for example, cylindrical lens, cross cylinder lens, rotary prism, or the like) disposed in the optical path L1 to rotate, the optical element is disposed at a rotational angle desired by the examiner in the optical path L1. The optical element disposed in the optical path L1 may be switched by an operation of an input unit (operation unit) such as the controller 4.

The lens disc 21R includes one lens disc or a plurality of lens discs as shown in FIG. 3. In a case where the plurality of lens discs are disposed, a plurality of drive units 22aR to 22dR are respectively provided to correspond to the lens discs. For example, each of the lens discs as a lens disc group includes an opening (or, 0D lens) and a plurality of the optical elements. The types of the lens disc may includes: a spherical lens disc which has a plurality of spherical lenses of different optical powers; a cylindrical lens disc which has a plurality of cylindrical lenses of different optical powers; and an auxiliary lens disc which has a plurality of types of auxiliary lenses. The auxiliary lens disc includes at least any one of a red filter/green filter, a prism, a cross cylinder lens, a polarizing plate, a Maddox lens, and an auto cross cylinder lens. The cylindrical lens may be disposed such that the drive unit 22aR can rotate the cylindrical lens about an axis of the optical path L1, and the rotary prism and the cross cylinder lens may be disposed such that drive units 23bR and 23cR can drive the rotary prism and the cross cylinder lens about an each axis thereof.

According to the above configuration, the correction optical system 20R for a right eye measurement can independently correct an individual reflection state such as a spherical power, a cylindrical power, a cylindrical axis, a prism value. Since the correction optical system 20L for a left eye measurement can be described similarly to the correction optical system 20R for a right eye examination, a description thereof will be omitted. A distance between the correction optical systems 20R and 20L may be adjustable so as to align with an interpupil distance PD of the subject eyes ER and EL.

In this case, a movement mechanism is provided in the lens discs 21R and 21L. The movement mechanism may move the lens discs 21R and 21L, and may adjust a relative distance therebetween. The interpupil distance PD is measured by an interpupil distance gauge or the like, and a measured result is input to the controller 4. The control unit 90 drives the movement mechanism to move the lens discs 21R and 21L such that the distance D and the interpupil distance PD coincide with each other. The apparatus 1 may be provided with an interpupil distance measurement unit.

<Relay Optical System>

As shown in FIG. 2, the relay optical system 30 may includes, for example, a half mirror 31, a concave mirror 32, a tracking mirror 33, a concave mirror 34, and a movement mechanism 35 which can move the tracking mirror 33 downward (in the Y direction). A drive unit 36 is provided to the movement mechanism 35 to move the tracking mirror 33 downward (in the Y direction).

The movement mechanism 35 is an optical path switch unit which switches an optical path to project a visual target light flux toward the subject eye E. For example, the movement mechanism 35 switches between a first optical path for projecting the visual target light flux toward the subject eye E from a horizontal direction, and a second optical path for projecting the visual target light flux toward the subject eye E from a direction which is tilted downward with respect to the horizontal direction. For example, the movement mechanism 35 changes a position of an optical member (tracking mirror 33 and the like) to switch the optical path of the visual target light flux.

The light flux passes through each of the correction optical systems 20R and 20L, passes through the half mirror 31, and is reflected and collected by the concave mirror 32. The light flux is reflected by the half mirror 31, and passes through the tracking mirror 33. The light flux passing through the tracking mirror 33 is reflected by the concave mirror 34. The reflected light is reflected by the tracking mirror 33, and reaches the subject eyes ER and EL, and forms an image of the visual target on both fundi of the subject eyes ER and EL.

Both of the light fluxes passing through the correction optical systems 20R and 20L are commonly relayed by the relay optical system 30, and images of the correction optical systems 20R and 20L are formed at an eyeglass wearing position (for example, approximately 12 mm from the corneal apex) of the subject eyes ER and EL. Accordingly, it is possible to have equivalent effects as if the correction optical systems 20R and 20L are disposed in front of the eye, and the subject person can collimate an image of the visual target in a natural state via the tracking mirror 33.

Accordingly, the subject person looks at the visual target in a natural vision state and responds to the examiner, so that the examiner can perform correction by the correction optical systems 20R and 20L until the eye-examination visual target can be appropriately seen, and a refractive power is measured based on the correction value.

<Detection Optical System>

As shown in FIG. 2, the detection optical system 40 includes an automatic tracking light source 41, a shielding plate 42, a flat mirror 43, a half mirror 44, a collective lens 45, a light receiving element 46, and the like. The detection optical system 40 detects a positional deviation of the subject eye E during an eye refracting power measurement. The detection optical system 40 detects deviations of the subject eye E and an image of the correction optical system 20. For example, the light source 41 is attached to a test frame 7 such that the light source 41 is disposed at a position where the subject person wears eyeglasses. The positional deviation of the subject eye E is detected based on a positional deviation of the light source 41. The shielding plate 42 has two open holes 42a and 42b. The holes 42a and 42b are provided to have a gap therebetween. A lid 47 is provided to close the hole 42b. A drive unit 48 may control the lid 47 such that the hole 42b can be opened and closed.

A light flux emitted from the light source 41 passes through the tracking mirror 33 and the holes 42a and 42b open in the shielding plate 42. The light flux passing through the hole 42a passes through the half mirror 44. Thereafter, the light flux is collected by the collective lens 45, and is received by the light receiving element 46. On the other hand, the light flux passing through the hole 42b is reflected by the flat mirror 43 and the half mirror 44. Accordingly, the light fluxes are collected by the collective lens 45, and are received by the light receiving element 46. A 2-dimensional sensor such as a CCD, a CMOS, or a position sensitive detector (PSD) may be used as the light receiving element 46.

An operation distance adjustment method of this illustrative embodiment will be described. In the apparatus 1, an operation distance for the subject eye E is set such that two light fluxes passing through the holes 42a and 42b are received by the light receiving element 46 while being combined. That is, the formation position of the image of the correction optical systems 20R and 20L is coincide with a position of a lens frame of the test frame 7 (for example, a position in front of the subject person by 12 mm from the corneal apex) in the Z direction (in a operation-distance direction).

This configuration is generally referred to as a range finder, and is used for adjusting a focus of a camera and the like. For example, in the operation distance adjustment method, the examiner operates the rotational knob 63 to protrude the contact portion 61 to a side of the subject person at the maximum. The examiner puts the test frame 7 on the subject person. The examiner instructs the subject person to put the forehead against the contact portion 61.

At this time, the light emitted from the light source 41 attached to the test frame 7 is separated by the holes 42a and 42b. Each of the separated light fluxes passes through the collective lens 45 and collected at a different position on a surface of the light receiving element 46.

The examiner operates the rotational knob 63 to gradually retract the contact portion 61 toward the apparatus 1. At the same time, the forehead of the subject person, the test frame 7, and the light source 41 also move toward the apparatus 1.

When a distance between the light source 41 and the apparatus 1 is appropriate, the light fluxes separated by the holes 42a and 42b are collected at the same position on the surface of the light receiving element 46.

At this time, the control unit 90 detects that the operation distance is appropriate based on a signal from the light receiving element 46, and sends a command signal to the notification unit 8. Once the notification unit 8 receives the command signal, the notification unit 8 notifies the examiner that a distance in the Z direction between the test frame 7 and the apparatus 1 is appropriate.

When the notification unit 8 operates, the examiner recognizes that the operation distance is appropriate. Accordingly, the examiner finishes operating the rotational knob 63, and completes the operation distance adjustment.

The light receiving element 46 is not limited to the 2-dimensional sensor, and for example, a 1-dimensional sensor such as a line sensor can be used. In this case, it is preferred that two 1-dimensional sensors be disposed to form at least a constant angle (preferably, 90 degrees). The light flux may be separated into two light fluxes by a separator lens such that the light fluxes are collected at the two sensors, respectively.

<Deviation Correction Unit>

The deviation correction unit 50 includes, for example, the tracking mirror 33 and a drive mechanism 51 (refer to FIG. 2). The tracking mirror 33 is disposed in a common optical path of the left and the right correction optical systems 20R and 20L. A formation position of the image of the correction optical systems 20R and 20L (optical elements disposed in the optical paths L1 and L2 thereof) is corrected by rotationally moving the tracking mirror 33.

The image of the correction optical systems 20R and 20L (optical elements disposed in the optical paths L1 and L2 thereof) is not physically an image formed by collecting light. That is, the formation position of the image of the correction optical systems 20R and 20L (optical elements disposed in the optical paths L1 and L2 thereof) is a conjugate position of the correction optical systems 20R and 20L with respect to the relay optical system 30.

The tracking mirror 33 may be an optical member such as a reflection member. The drive mechanism 51 can preferably change an orientation of a mirror surface of the tracking mirror 33. The drive mechanism 51 may employ, for example, a rotational mechanism which has a rotation axis in the horizontal direction and a vertical direction, or any one of them.

The deviation correction unit 50 drives, for example, an optical member such as the tracking mirror 33, and deflects an apparent light flux for forming the image of the correction optical systems 20R and 20L (optical elements disposed in the optical paths L1 and L2). Accordingly, the deviation correction unit 50 optically corrects a position where the image of the correction optical systems 20R and 20L (optical elements disposed in the optical paths L1 and L2) is formed to be located in front of the subject eye E. For example, the position in front of the subject eye E is a wearing position of eyeglasses of the subject eyes E.

The drive mechanism 51 includes a drive unit (for example, voice coil motor mechanism) 52, and may rotate the tracking mirror 33 about the horizontal rotary axis and the vertical rotary axis. That is, the drive unit 52 may rotate the tracking mirror 33 in XY directions. A plurality of reflection mirrors for a deviation correction may be provided (for example, galvano motor mechanism is used), and at this time, one reflection mirror may be rotated in the X direction, and another reflection mirror may be rotated in the Y direction.

<Control System>

Figure 4:
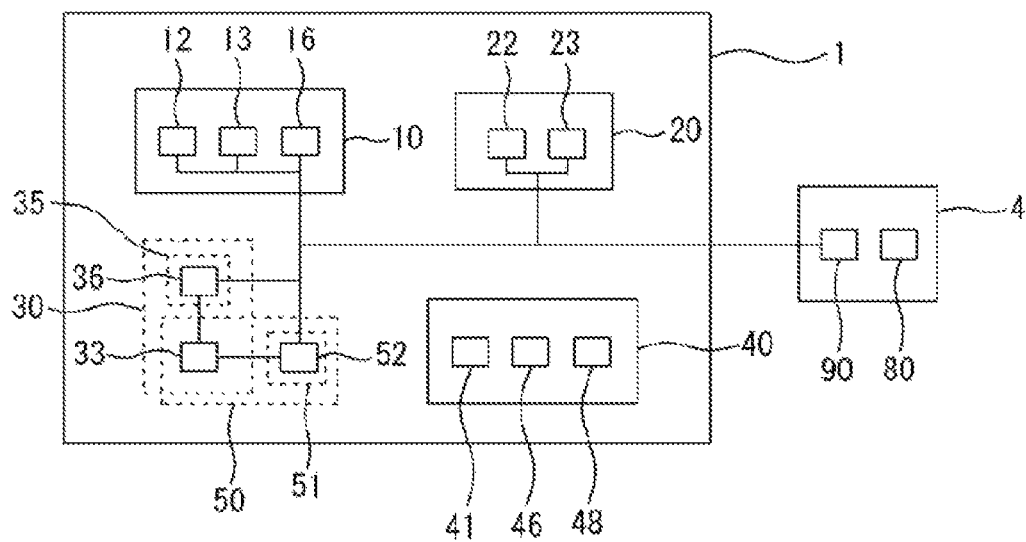
FIG. 4 is a block diagram showing a control system of the subjective eye refracting power measurement apparatus according to the illustrative embodiment.

FIG. 4 is a block diagram showing a control system of the illustrative embodiment. The control unit 90 provided in the controller 4 may be connected to the light source 12, the display 13, and the drive unit 16 of the visual target projection optical system 10; the drive units 22 and 23 of the correction optical system 20; the drive unit 36 of the relay optical system 30; the light source 41, the light receiving element 46, and the drive unit 48 of the detection optical system 40; the drive unit 52 of the deviation correction unit 50; a memory 80 of the controller 4; and the like. The control unit 90 receives a light reception signal from the light receiving element 46. The control unit 90 controls the drive unit 52 based on the light reception signal to control the orientation of the tracking mirror 33.

<Method for Controlling Tracking Mirror>

Figure 5A:
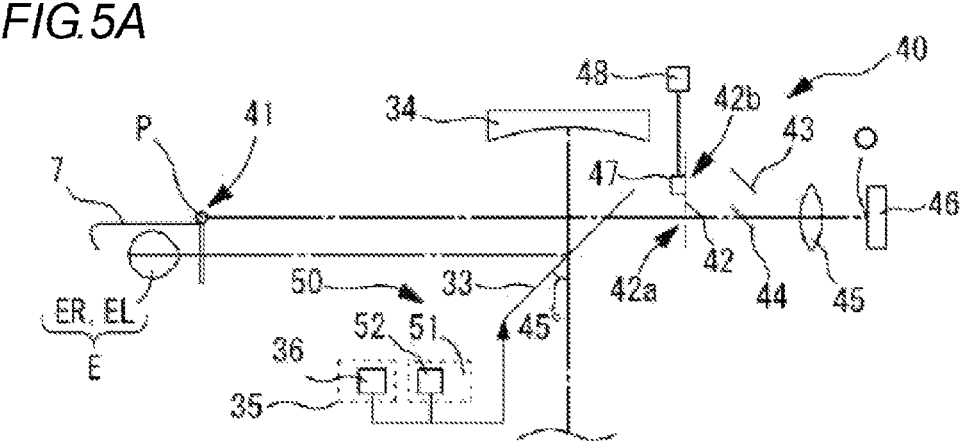
FIGS. 5A, 5B and 5C are views showing a deviation correction unit of the subjective eye refracting power measurement apparatus according to the illustrative embodiment.
Figure 5B:
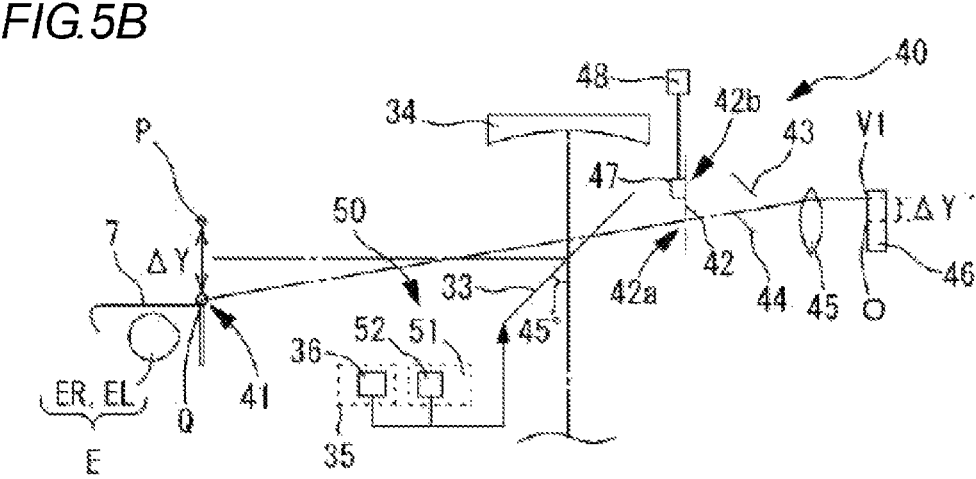
Figure 5C:
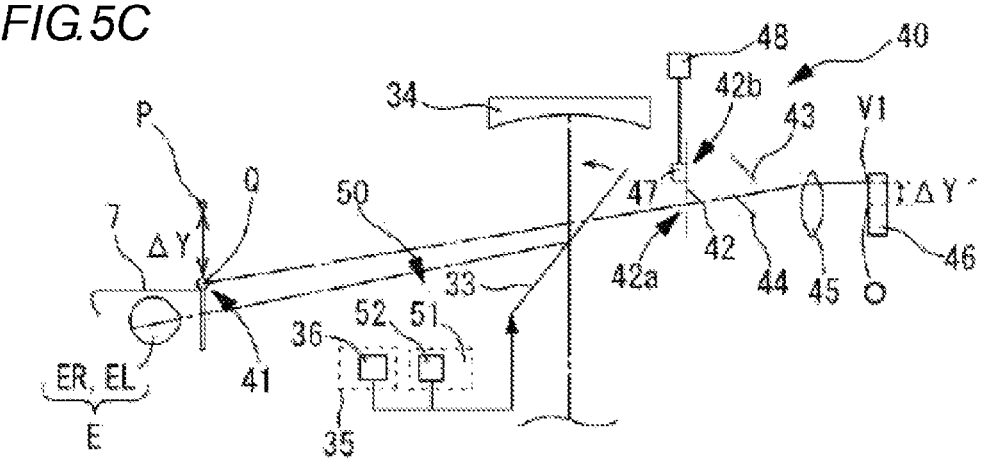

A method for controlling the tracking mirror 33 will be described. FIGS. 5A, 5B and 5C show an example in which a positional deviation of the subject eye E during an eye examination is corrected in the apparatus according to the illustrative embodiment. FIG. 5A shows a state before a position of the subject eye E deviates. FIG. 5B shows a state immediately after the position of the subject eye E deviates in the Y direction. FIG. 5C shows a state after an angle of the tracking mirror 33 is corrected for the deviation. The subject eye E and the light source 41 are assumed to move in an integral manner. The hole 42b is closed by the lid 47 during the eye examination.

As shown in FIG. 5A, the light source 41 is located at a reference position P, and the tracking mirror 33 takes a reference posture (for example, inclined 0° in the X direction and inclined 45° in the Y direction). In a state where the light source 41 is located at the position P, the image of the correction optical system 20 is formed in front of the subject eye E. Accordingly, an image of the visual target light flux incident on the subject eye E is formed at an appropriate position with respect to the subject eye E. The light flux emitted from the light source 41 at the position P passes through the tracking mirror 33, the hole 42a, the half mirror 44, and the collective lens 45, and is collected at a reference point O on the surface of the light receiving element 46. The light receiving element 46 transmits a light reception signal to the control unit 90. Based on the light reception signal, the control unit 90 obtains position information of the reference point O. The position information of the reference point O is stored in the memory 80.

As shown in FIG. 5B, the light source 41 moves to a position Q which deviates by $\Delta Y$ in the Y direction. In a state before the angle of the tracking mirror 33 is corrected, the image of the correction optical system 20 is formed at a position deviating from the front of the subject eye. That is, an image of the visual target light flux incident on the subject eye E is formed at an inappropriate position with respect to the subject eye E. At this time, the light flux emitted from the light source 41 at the position Q passes through the tracking mirror 33, the hole 42a, the half mirror 44, and the collective lens 45, and is collected at a point V1 on the surface of the light receiving element 46. The point V1 is positioned to deviate by $\Delta Y'$ in the Y direction from the reference point O. The light receiving element 46 transmits a light reception signal at this time to the control unit 90. Based on the light reception signal, the control unit 90 detects the amount and a direction of deviation of the point V1 with respect to the reference point O.

Based on the light reception signal from the light receiving element 46, the control unit 90 controls the drive unit 52. As an example of the control method, based on the deviation amount $\Delta Y'$ and the deviation direction, the control unit 90 may drive the tracking mirror 33 by the drive amount stored in the memory 80 in advance, and may change the direction. The memory 80 stores an angle θ in advance which corresponds to the deviation amount ΔY', for example, an angle θ1° is stored when the point V1 deviates by ΔY'1 from the reference point O; an angle θ2° is stored when the point V1 deviates by ΔY'2 from the reference point O; or an angle θ3° is stored when the point V1 deviates by ΔY'3 from the reference point O. The angle θ° (the amount of rotation and a direction of rotation) corresponding to the deviation amount ΔY may be obtained by calculation or obtained experimentally. The control unit 90 obtains the deviation amount ΔY' based on the light reception signal from the light receiving element 46, and rotates the tracking mirror 33 by the angle θ° which is stored in the memory 80 for the deviation amount ΔY'. Accordingly, the control unit 90 performs a correction such that the image of the correction optical system 20 is formed in front of the subject eye E. Accordingly, an image of the visual target light flux incident on the subject eye E is formed at an appropriate position. As such, when the position of the subject eye E deviates, the tracking mirror 33 is rotated to correct a position where the image of the correction optical system 20 is formed, and thus, the visual target is appropriately presented to the subject eye E.

The amount and a direction of driving the tracking mirror 33 are determined based on the deviation of the point V1 from the reference point O, or may be determined based on the position information (address) of the point V1. Even in this method, when the position of the subject eye E deviates, the visual target is appropriately presented to the subject eye E.

The method for controlling the tracking mirror 33 when a position deviates in the Y direction is described above. Even in a case where a position deviates in the X direction, the similar control method is used, and thus, a description thereof is omitted.

<Sequence and Operation of Far Distance Examination>

A sequence of a far distance examination of the subject eye E using the apparatus 1 of the illustrative embodiment will be described together with an operation of the apparatus 1. First, the examiner operates the controller 4, sets a measurement mode to a far distance measurement mode, and presents a desired far distance examination visual target on the window 3. Subsequently, the examiner puts the test frame 7 on the subject person. The examiner instructs the subject person to put the forehead against the forehead rest 60, and to observe the presentation window 3. Until the notification unit 8 operates (for example, until a lamp is illuminated), the examiner operates the rotational knob 63 to adjust a position of the forehead rest 60 in an operation-distance direction. When an adjustment of the position of the forehead rest 60 is completed, the examiner operates the controller 4 in order for the lid 47 to close the hole 42b. The control unit 90 controls the drive unit 48 in order for the lid 47 to close the hole 42b. Accordingly, only the light flux passing through the hole 42a is received by the light receiving element 46. The light flux passing through the hole 42a is used for detecting an eye position in the XY directions.

Figure 6:
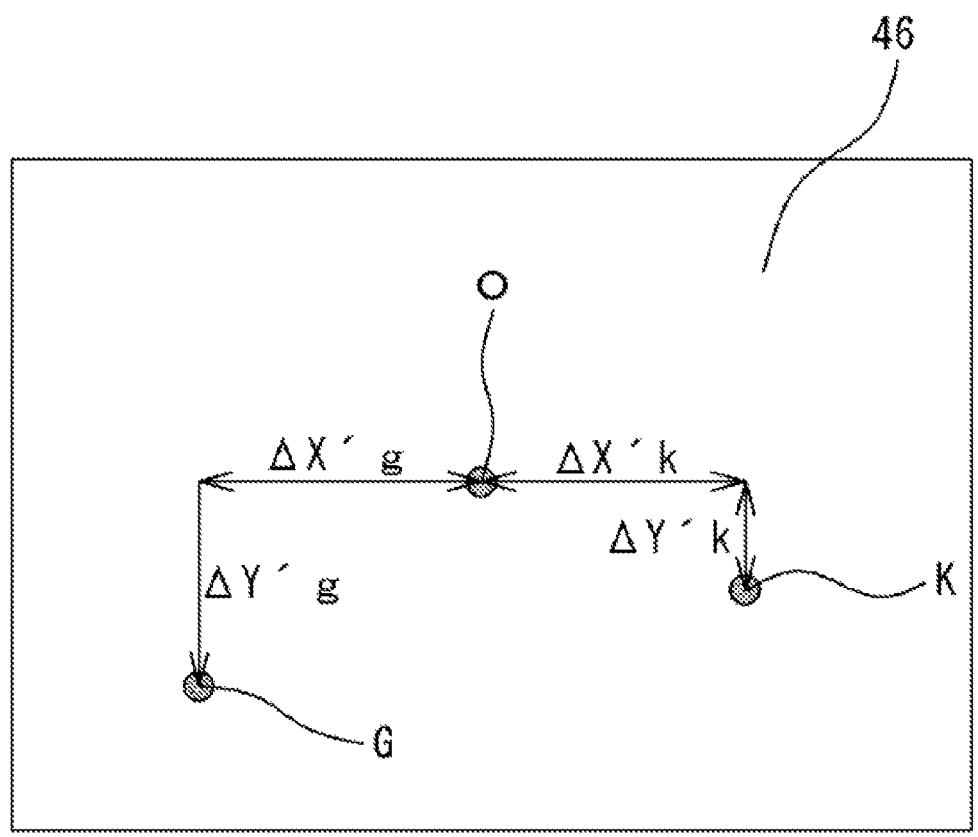
FIG. 6 is a view showing a change of a collecting position on a light receiving element of the subjective eye refracting power measurement apparatus according to the illustrative embodiment.

Subsequently, the eye position in the XY directions is detected. For example, the light flux passing through the hole 42a from the light source 41 passes through the half mirror 44 and the collective lens 45, and is collected at a point G on the surface of the light receiving element 46 (refer to FIG. 6). The light receiving element 46 sends a light reception signal at this time to the control unit 90. The control unit 90 receives the light reception signal to calculate the amounts ΔX'g and ΔY'g and a direction of deviation of the point G with respect to the reference point O.

When a detection of the eye position in the XY directions is completed, based on the deviation amounts ΔX'g and ΔY'g, the control unit 90 reads a rotation angle θX° of the tracking mirror 33 in the X direction and the rotation direction, and a rotation angle θY° of the tracking mirror 33 in the Y direction and the rotation direction from the memory 80. The control unit 90 controls the drive unit 52 to change the orientation of the tracking mirror 33. By changing the orientation of the tracking mirror 33, the control unit 90 performs a correction such that the image of the correction optical system 20 is formed in front of the subject eye E. Accordingly, an image of the visual target light flux incident on the subject eye E is formed at an appropriate position with respect to the subject eye E.

After the eye-examination visual target can be presented to the subject eye E according to the operation described above, the examiner starts performing the far distance examination. The examiner instructs the subject person to look at the visual target in a natural vision state, and asks the visibility of the visual target. The examiner performs a correction by the correction optical systems 20R and 20L until the eye-examination visual target can be appropriately seen, and a refractive power is measured based on the correction value.

There is a case where a posture of the subject person changes, and a position of the subject eye E deviates during an examination. In this case, since the image of the correction optical system 20 is formed at a position deviating from the front of the subject eye E, the subject person cannot appropriately observe the eye-examination visual target. When the position of the subject eye E deviates, the position of the light source 41 deviates. When the position of the light source 41 deviates, the light flux from the light source 41 is collected at a deviated position on the surface of the light receiving element 46.

For example, a point K is taken as the deviated position. The light receiving element 46 sends a light reception signal at this time to the control unit 90. The control unit 90 receives the light reception signal to calculate the amounts ΔX'k and ΔY'k and a direction of deviation of the point K with respect to the reference point O. Based on the amounts ΔX'k and ΔY'k and the direction of deviation, the control unit 90 reads a rotation angle θX° of the tracking mirror 33 in the X direction and the rotation direction, and a rotation angle θY° of the tracking mirror 33 in the Y direction and the rotation direction from the memory 80. The control unit 90 controls the drive unit 52 to change an orientation of the tracking mirror 33. By changing the orientation of the tracking mirror 33, the control unit 90 performs a correction such that the image of the correction optical system 20 is formed in front of the subject eye E. That is, the positional deviation of the subject eye E during an eye refracting power measurement is detected, and an image formation position is corrected such that the image of the correction optical system 20 is correctly positioned in front of the subject eye E. Accordingly, an image of the visual target light flux incident on the subject eye E is formed at an appropriate position with respect to the subject eye E.

According to the above configuration, even though the position of the subject eye E during an eye examination deviates, and the image of the correction optical system 20 is formed at a position deviating from the front of the subject eye E, it is possible to form the image of the correction optical system 20 in front of the subject eye E again. That is, the visual target is appropriately presented to the subject eye E. Accordingly, the subject person does not observe an inappropriate visual target caused by a deviation of the position of the subject eye E. The subject person can take an eye examination in a comfortable posture without maintaining a constant posture. Further, it is not necessary for the examiner to adjust the position of the apparatus or the subject person while confirming the positional deviation of the subject eye E.

<Sequence and Operation of Near Distance Examination>

Figure 7:
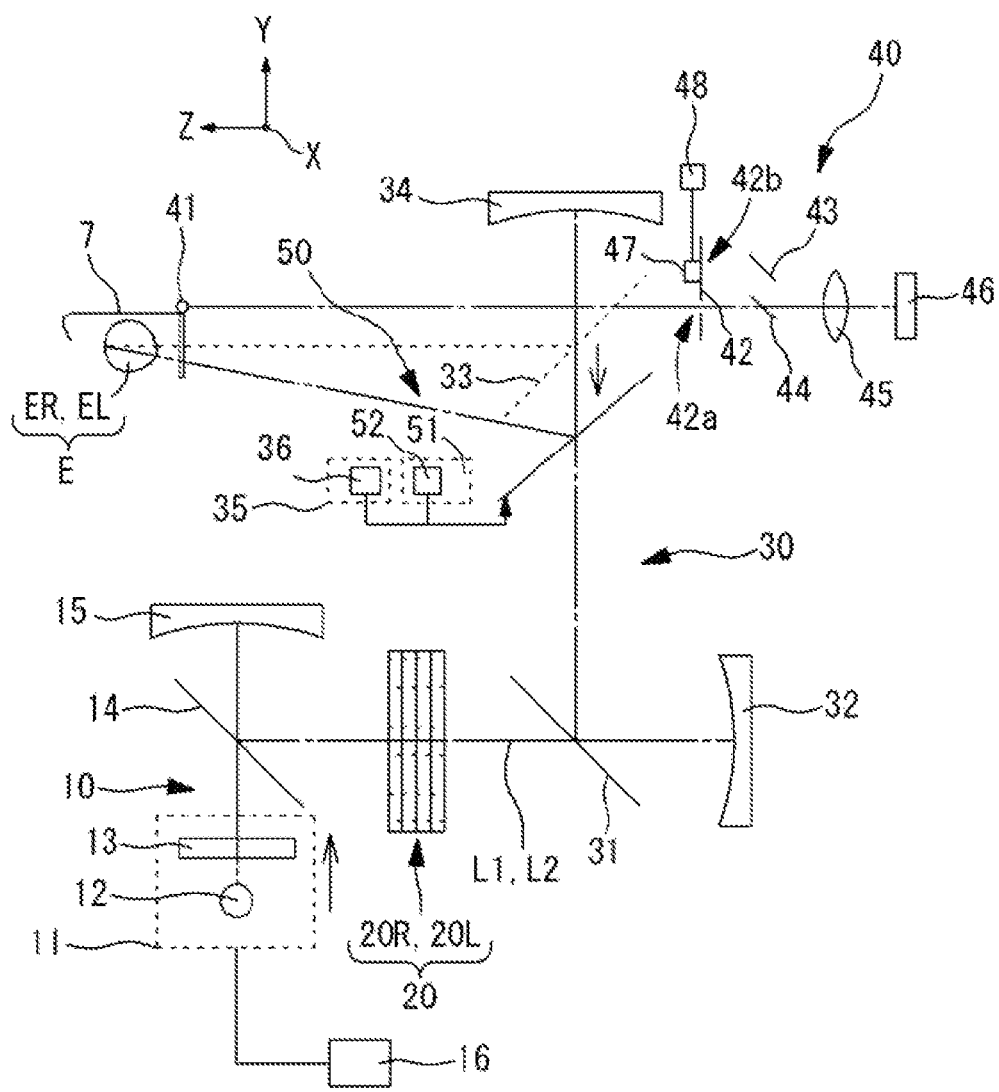
FIG. 7 is a schematic view showing a configuration of the optical system of the illustrative embodiment when a near distance examination is performed.

A sequence of a near distance examination will be described together with an operation of the apparatus 1. FIG. 7 is a schematic view showing an arrangement of the optical system when a near distance examination is performed. The examiner operates the controller 4 to set a measurement mode to a near distance measurement mode. When a measurement mode is set to the near distance measurement mode, the control unit 90 controls the drive unit 16 to move the visual target projection unit 11 (for example, light source 12 and display 13) toward the concave mirror 15. It is possible to present the eye-examination visual target at a distance for a near distance examination (for example, 40 mm from the front of the subject eye E) by changing a length of the optical path. In a case where the distance for a near distance examination is set to be short, it is considered to replace the half mirror 14 and the concave mirror 15 with convex lenses. In this configuration, in a case where the distance for a far distance examination is switched to the distance for a near distance examination for presenting the visual target, the visual target projection unit 11 is preferably located closer to the convex lens. JP-A-59-85642 should be referred to for this configuration.

When the visual target projection unit 11 moves, optical powers of the correction optical systems 20R and 20L change. Therefore, the optical powers of the correction optical system 20R and 20L are preferably corrected based on a movement distance of the visual target projection unit 11. For example, when a measurement mode is set to be the near distance measurement mode, the control unit 90 sets a state where a spherical lens having a refractive power of +10 diopters is disposed in the optical paths L1 and L2 to a state where a refractive power is 0 diopters (in a non-correction state), and an eye examination may be performed. Accordingly, it is possible to perform any of a far distance examination and a near distance examination using the same correction optical system 20 without switching the correction optical system 20 for a far distance examination to the correction optical system 20 for a near distance examination, and vice versa.

When a measurement mode is set to be the near distance measurement mode, the control unit 90 controls the drive unit 36 to move the position of the tracking mirror 33 downward (in the Y direction) with respect to the subject eye E. Since the tracking mirror 33 moves downward, the relay optical system 30 projects the visual target light flux toward the subject eye E from the bottom compared to when the far distance examination is performed. The subject person tilts the visual line of the eyes downward from the horizontal direction so as to observe the eye-examination visual target.

Since a sequence of the eye examination and an operation of the apparatus thereafter are the same as those of the far distance examination, a description thereof will be omitted. In a case where the tracking mirror 33 moves downward (in the Y direction), the length of the optical path changes, and thus, refraction degree of the light flux reaching the subject eye E changes. In this case, it is preferable to adjust an operation distance of the forehead rest 60 again when a near distance examination is performed.

In general, when a person naturally looks at something which is near, the person tilts the visual line downward from the horizontal direction. As described above, the tracking mirror 33 moves downward, the subject person tilts the visual line downward from the horizontal direction, and thus, it is possible to perform the near distance examination for the subject person in a state much closer to natural vision.

As described also in the near distance examination, the detection optical system 40 and the deviation correction unit 50 can perform a correction such that the image of the correction optical system 20 is formed in front of the subject eye E.

For example, when the near distance examination is performed, there is a case where the subject person leans the head forward to tilt the visual line downward. In this case, there is a case where it is difficult to detect the subject eye E from a specific direction (for example, the horizontal direction with respect to the subject eye E). For example, the subject eye E may be hidden by the eyelid.

The detection optical system 40 of this illustrative embodiment detects the light source 41 of the test frame 7 put on the subject person so as to detect a positional deviation of the subject eye E. It is possible to detect the position of the test frame 7 even though a situation changes, for example, the subject person leans the head. As such, even though it is difficult to detect the subject eye E, it is possible to detect the positional deviation of the subject eye E by detecting the position of the test frame 7 which the subject person wears.

The detection optical system 40 of this illustrative embodiment detects the position of the test frame 7. However, the present disclosure is not limited to this illustrative embodiment. For example, the detection optical system 40 may detect a characteristic portion such as the nose or the mouth, as long as the positional deviation of the subject eye E can be detected based on the detected result.

That is, the detection optical system 40 may have any configuration as long as the position and the positional deviation of the subject eye E and the like can be detected. Of course, in a technique for detecting the positional deviation of the subject eye E or the like, the positional deviation may be detected by directly detecting the position of the subject eye E.

Figure 8A:
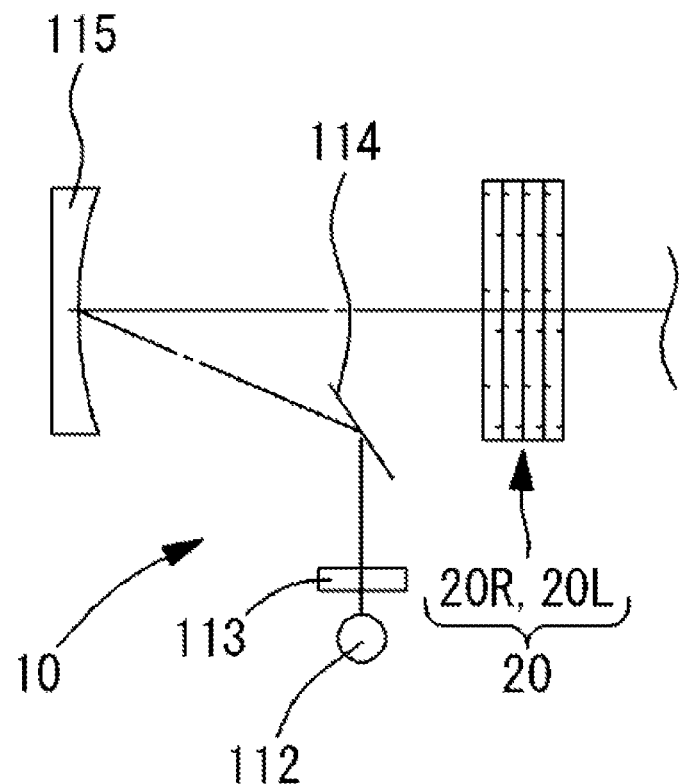
FIGS. 8A and 8B are views showing modified illustrative embodiments.

The configuration of the visual target projection system 10 is not limited to the above-described illustrative embodiment. For example, as shown in FIG. 8A, the visual target projection system 10 may include a light source 112, a display 113, a reflection member 114, and a concave mirror 115. A light flux from the light source 112 projects a display of the display 113, and the light flux is reflected by the reflection member 114 and is diagonally incident on the concave mirror 115. The light flux is reflected by the concave mirror 115, and the light flux moves forward on an optical axis of the concave mirror 115 and passes through the correction optical systems 20R and 20L. Since an optical path thereafter is the same as that in the above-described illustrative embodiment, a description thereof will be omitted.

As described above, since the visual target projection system 10 has a configuration in which the visual target light flux is incident on the concave mirror 115 from outside of the optical axis of the concave mirror 115, it is possible to remove the half mirror 14 of the visual target projection system 10 from the configuration. Whenever a light flux passes through or is reflected by a half mirror, since light amount decreases, it is possible to maintain the light amount of the visual target light flux by a removal of the half mirror.

Figure 8B:
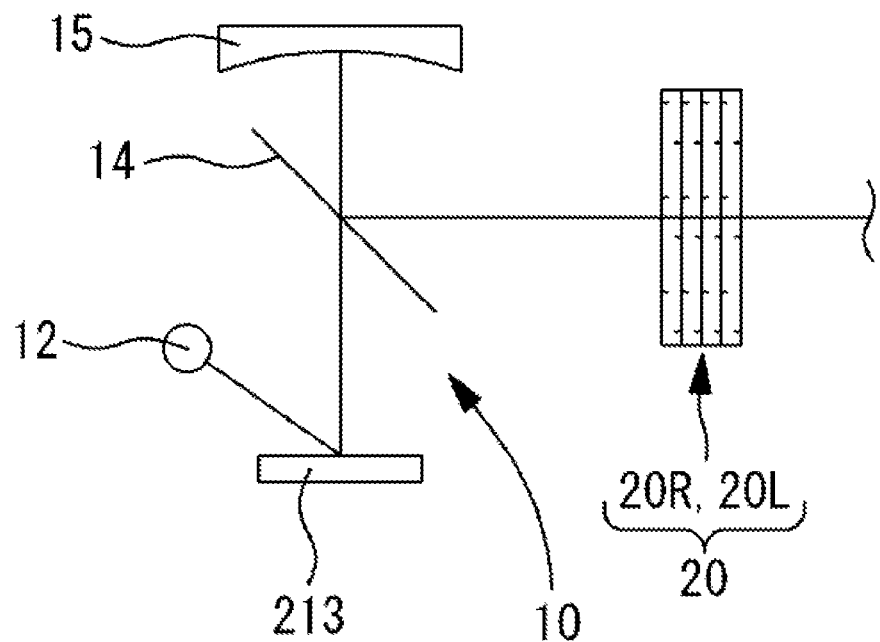

As shown in FIG. 8B, the visual target projection system 10 may use a digital micromirror device (DMD) 213 instead of the liquid crystal display 13. In general, the DMD 213 has a high reflectivity and is clean. Therefore, compared to when the polarizing liquid crystal display 13 is used, it is possible to maintain the light amount of the visual target light flux.

Figure 9A:
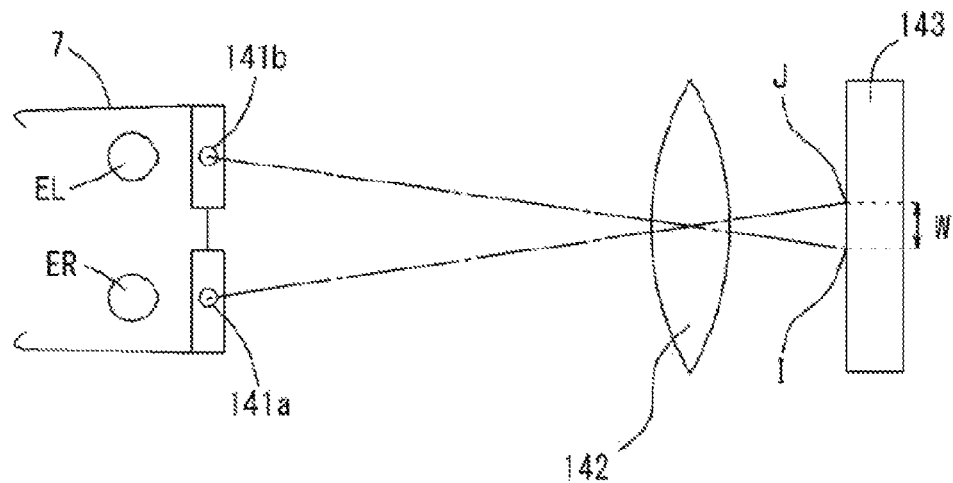
FIGS. 9A and 9B are views showing a detection optical system according to a modified illustrative embodiment.

The configuration of the detection optical system 40 is not limited to that of the above-described illustrative embodiment. For example, as shown in FIG. 9A, the detection optical system 40 may include two light sources 141a and 141b which are attached to the test frame 7, a collective lens 142, and a light receiving element 143. Light fluxes from the light sources 141a and 141b are collected at different positions on a surface of the light receiving element 143. For example, the light fluxes are collected at points I and J. A distance W between the two points I and J is changed by a distance in the Z direction (in the operation-distance direction) between the light sources 141a and 141b and the apparatus 1.

Accordingly, it is possible to adjust operation distances of the forehead rest 60 and the subject eye E such that the distance W between the two points becomes a preset distance. In this configuration, when the subject eye E is close to the apparatus 1, the distance W becomes larger, and when the subject eye E is far from the apparatus 1, the distance W becomes smaller. Accordingly, the control unit 90 may calculate a distance between the subject eye E and the apparatus 1 based on the measurement of the distance W. A drive unit may be provided such that the control unit 90 automatically adjusts the position of the forehead rest 60 based on the calculated distance. A notification unit may be provided to notify the subject person that the subject eye E is close to or far from the apparatus 1.

Similarly to the above-described illustrative embodiment, it is possible to detect the position of the subject eye E in the XY directions. For example, it is possible to detect the position of the subject eye E in the XY directions based on the amount and a direction of deviation of the point I from a reference point.

That is, the detection optical system 40 may have any configuration as long as the position and the positional deviation of the subject eye E can be obtained.

Figure 9B:
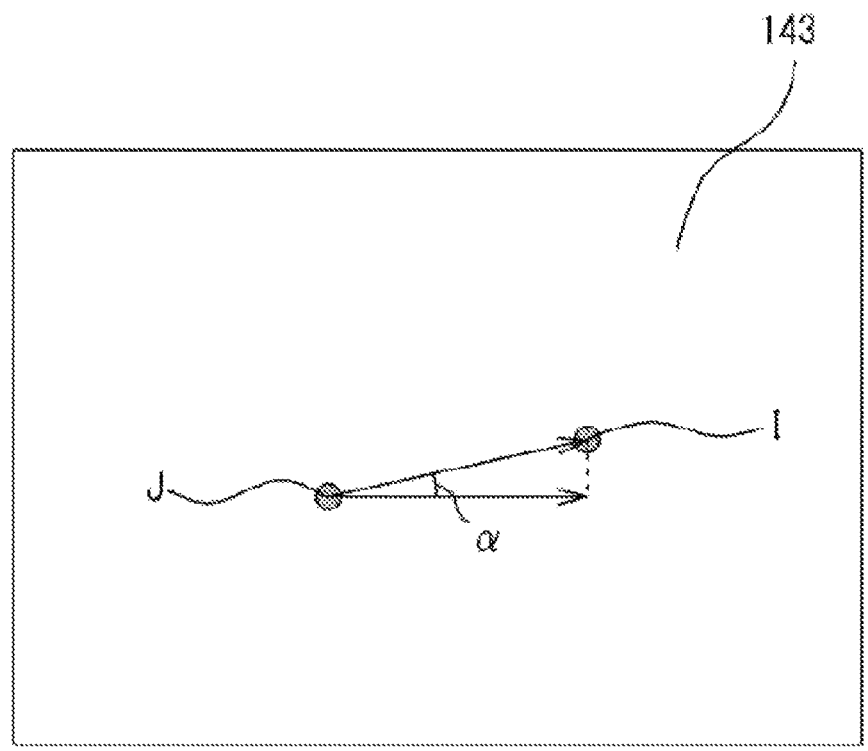

Alternatively, a tilt of the test frame 7 may be detected based on the positions of the points I and J. For example, as shown in FIG. 9B, a tilt α of the two points may be detected, and based on the detected result, the tilt of the test frame 7 may be detected. The tilt of the test frame 7 is detected, and thus, a tilt of the left and right eyes EL and ER of the subject person is detected. That is, the detection optical system 40 operates as a tilt detector which detects the tilt of the subject eyes EL and ER.

When the left and right eyes EL and ER of the subject person tilt, the image of the correction optical system 20 is formed at a position deviating from the front of the subject eye E. Accordingly, when the detection optical system 40 detects the tilt of the left and right eyes EL and ER of the subject person, the control unit 90 operates the notification unit 8. Then, the notification unit 8 may notify the subject person that the eye-examination visual target is not appropriately presented. The examiner confirms that the notification unit 8 is operated, and instructs the subject person not to lean the head to a side.

That is, the apparatus may include a detection unit (for example, a detection optical system 40) which detects the tilt of the left and right eyes EL and ER of the subject person, and a notification unit (for example, notification unit 8) which notifies the result.

Figure 10A:
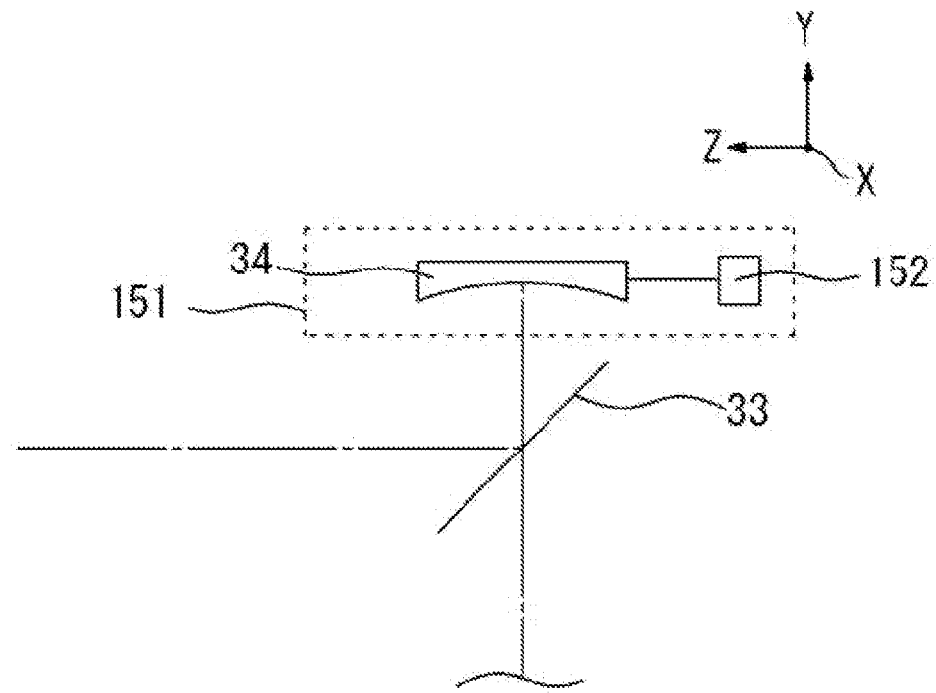
FIGS. 10A and 10B are views showing a deviation correction unit according to a modified illustrative embodiment.
Figure 10B:
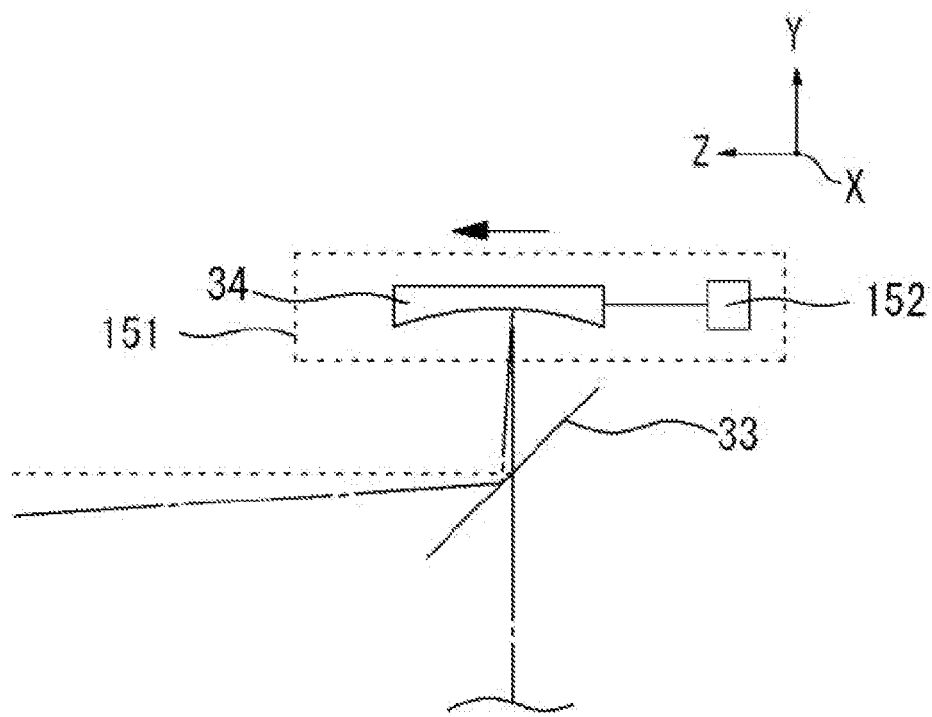

The configuration of the deviation correction unit 50 is not limited to that of the above-described illustrative embodiment. For example, as shown in FIGS. 10A and 10B, the deviation correction unit 50 may have the above-described configuration and a movement mechanism 151 further provided to move the concave mirror 34. The movement mechanism 151 includes a drive unit 152 and the like.

When the movement mechanism 151 moves the concave mirror 34 in XZ directions, a formation position of an image of the correction optical system 20 changes. In this way, based on the deviation of the subject eye E detected by the detection optical system 40, the control unit 90 controls the movement mechanism 151 to perform a correction such that the image of the correction optical system 20 is formed in front of the subject eye E. Accordingly, the visual target is appropriately presented to the subject eye E.

Figure 11A:
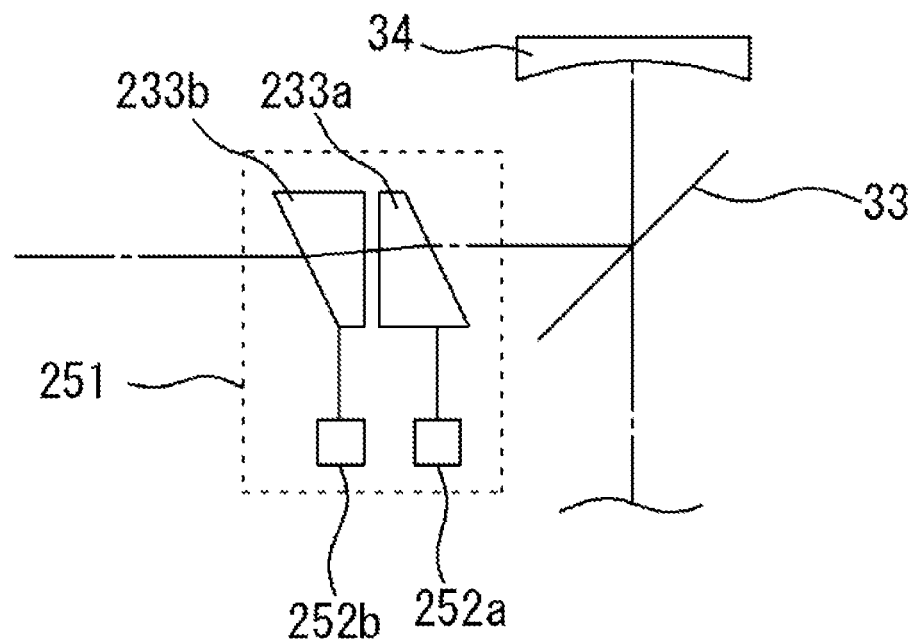
FIGS. 11A and 11B are views showing a deviation correction unit according to a modified illustrative embodiment.
Figure 11B:
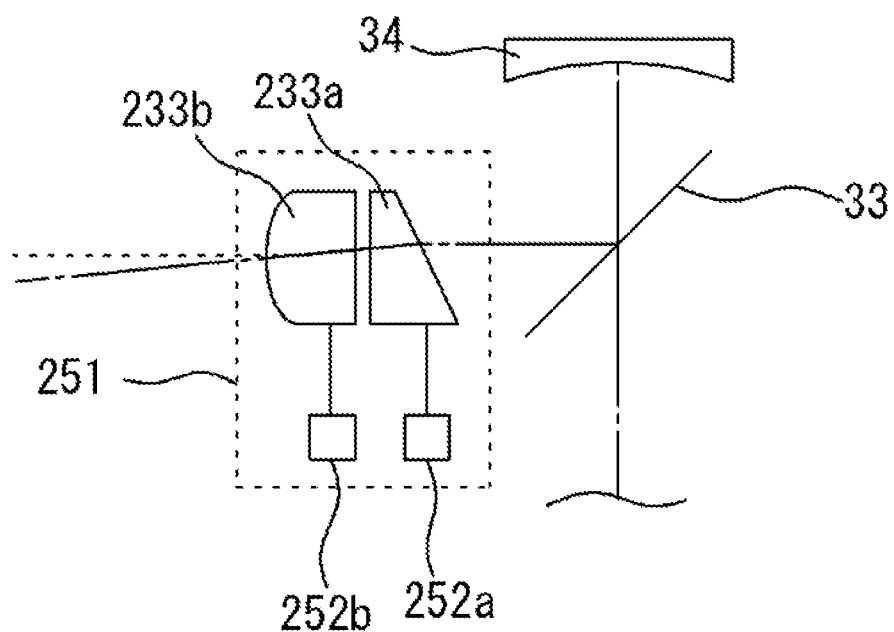

As shown in FIGS. 11A and 11B, the deviation correction unit 50 may have the above-described configuration, and further have rotary prisms 233a and 233b, and a movement mechanism 251. The movement mechanism 251 includes drive units 252a and 252b. The visual target light flux from the light source 12 passing through the correction optical systems 20R and 20L passes through the rotary prisms 233a and 233b via the relay optical system 30, and is incident on the subject eye E. When the movement mechanism 251 rotates each of the rotary prisms 233a and 233b, the formation position of the image of the correction optical system 20 changes. In this way, the movement mechanism 251 performs a correction such that the image of the correction optical system 20 is formed in front of the subject eye E. FIGS. 11A and 11B show a state before the rotary prism 233b rotates 90° (refer to FIG. 11A), and a state after the rotary prism 233b rotates 90° (refer to FIG. 11B).

That is, the deviation correction unit 50 may change an optical path of the visual target light flux by the optical member. When the rotary prisms 233a and 233b are used, there is a case where the light flux from the light source 41 is affected by the rotary prisms 233a and 233b and the like, until the light flux reach the light receiving element 46. Therefore, the detection optical system 40 is preferably disposed at a position where the detection optical system 40 is not affected by the rotary prisms 233a and 233b and the like. For example, a light receiving system such as the shielding plate 42, the flat mirror 43, the half mirror 44, the collective lens 45, and the light receiving element 46 may be disposed above the half mirror 33 and closer to a side of the subject person than the concave mirror 34, or may be disposed outside of the housing 2.

Further, as a modified illustrative embodiment, it is consider that a position where the image of the visual target light flux is formed is corrected based on the deviation of the subject eye E in the Z direction during an eye examination. In this case, it is preferred that each of the correction optical systems 20R and 20L be configured to have Alvarez lens.

The Alvarez lens is configured to have two optical elements (for example, phase contrast plate or the like), each of which has a special aspherical surface on one side and a flat surface on the other side. The two optical elements are disposed to have the aspherical surfaces facing each other, both of the optical elements are displaced (moved) by the same displacement (the amount of movement) in opposite directions with each thereof rotating 180°, and thus it is possible to continuously change a refracting power (refer to U.S. Pat. No. 3,305,294).

The detection optical system 40 detects the deviation of the subject eye E in the Z direction, and based on the detected result, moves the visual target projection system 10 with respect to the concave mirror 14. At the same time, it is preferred that the two optical elements of the Alvarez lens be displaced such that a change in an optical power of the light flux is corrected.

Accordingly, it is possible to correct the formation position of the image of the correction optical system 20 based on the deviation of the subject eye E in the Z direction during an eye examination.

In the above-described apparatus 1, the controller 4 includes the control unit 90. However, the present disclosure is not limited to this configuration. The control unit may be provided in the housing 2. Alternatively, the control unit may be provided in each of the controller 4 and the housing 2. The control unit may be connected to each of configuration elements by a wire or a wireless system.

What is claimed is:

1. A subjective eye refracting power measurement apparatus configured to measure a refracting power of a subject eye, the apparatus comprising:
   a projection optical system configured to project a visual target light flux toward the subject eye to form an eye-examination visual target on a fundus of the subject eye;
   a correction optical system disposed in an optical path of the projection optical system and configured to change a refracting power thereof;
   a relay optical system comprising a concave mirror, the relay optical system configured to relay a light flux passing through the correction optical system and to form an image of the correction optical system in front of the subject eye;
   a deviation detector configured to detect a positional deviation of the image of the correction optical system with respect to the subject eye; and
   a correction unit configured to optically correct a formation position of the image of the correction optical system based on a detection result by the deviation detector such that the image of the correction optical system is formed in front of the subject eye.

2. The subjective eye refracting power measurement apparatus according to claim 1,
   wherein the correction unit includes a drive unit configured to drive an optical member disposed between the correction optical system and a subject person, and
   wherein the correction unit is configured to control the drive unit and cause the an apparent light flux for forming the image of the correction optical system in front of the subject eye to be deflected, to thereby optically correct the formation position of the image.

3. The subjective eye refracting power measurement apparatus according to claim 1,
   wherein the deviation detector includes a light receiving element configured to receive a light from a light emitting source provided to a subject person, and
   wherein the deviation detector is configured to detect the positional deviation based on a light reception signal of the light receiving element.

4. The subjective eye refracting power measurement apparatus according to claim 2,
   wherein the correction optical system includes a pair of a correction optical system for a right eye and a correction optical system for a left eye,
   wherein the relay optical system is configured to commonly relay light fluxes passing through the pair of correction optical systems, and
   wherein the optical member is disposed in a common optical path of the correction optical systems for a right eye and a left eye, in the relay optical system.

5. The subjective eye refracting power measurement apparatus according to claim 2,
   wherein the optical member is a light reflection member, and
   wherein the correction unit is configured to control the drive unit to change an angle of the light reflection member, to thereby optically correct the formation position of the image.

6. The subjective eye refracting power measurement apparatus according to claim 2,
   wherein the optical member is a concave mirror, and
   wherein the correction unit is configured to move the concave mirror to correct the formation position of the image.

7. The subjective eye refracting power measurement apparatus according to claim 2,
   wherein the optical member is a prism, and
   wherein the correction unit is configured to move the prism to correct the 30 formation position of the image.

8. The subjective eye refracting power measurement apparatus according to claim 1, further comprising:
   a tilt detector configured to detect a tilt of left and right subject eyes; and
   a notification unit configured to notify a detection result by the tilt detector.

9. A subjective eye refracting power measurement apparatus configured to measure a refracting power of a subject eye, the apparatus comprising:
   a projection optical system configured to project a visual target light flux toward the subject eye to form an eye-examination visual target on a fundus of the subject eye;
   a correction optical system disposed in an optical path of the projection optical system and configured to change a refracting power thereof;
   a relay optical system comprising a concave mirror, the relay optical system configured to relay a light flux passing through the correction optical system and to form an image of the correction optical system in front of the subject eye;
   a distance change unit configured to optically change a presentation distance of the visual target between for a far distance examination and for a near distance examination; and
   an optical path switch unit configured to switch between a first optical path for projecting the visual target light flux toward the subject eye from a horizontal direction and a second optical path for projecting the visual target light flux toward the subject eye from a direction which is tilted downward with respect to the horizontal direction.

10. The subjective eye refracting power measurement apparatus according to claim 9
    wherein the optical path switch unit includes a drive unit configured to drive an optical member disposed between the correction optical system and a subject person with respect to the correction optical system, to thereby switch between the first optical path and the second optical path.

11. The subjective eye refracting power measurement apparatus according to claim 10
    wherein the optical member is a light reflection member configured to reflect the visual target light flux toward the subject eye, and
    wherein the drive unit is configured to move the light reflection member downward to switch between the first optical path and the second optical path.

12. The subjective eye refracting power measurement apparatus according to claim 9, further comprising:
    a control unit configured to, when performing a near distance examination while the distance change unit changes the presentation distance of the visual target, change an optical power setting of the correction optical system from that for a far distance examination.

13. The subjective eye refracting power measurement apparatus according to claim 9, further comprising:
a deviation detector configured to detect a positional deviation of the image of the correction optical system with respect to the subject eye.

14. The subjective eye refracting power measurement apparatus according to claim 13,
wherein the deviation detector is configured to, at least when performing a near distance examination, detect at least one of a characteristic portion of a subject person other than the subject eye and a frame which the subject person wears, to thereby detect the positional deviation.

15. The subjective eye refracting power measurement apparatus according to claim 9,
wherein the optical path switch unit is configured to switch between the first optical path and the second optical path in conjunction with a change of the presentation distance by the distance change unit.

16. The subjective eye refracting power measurement apparatus according to claim 1, wherein the correction optical system comprises an optical unit arranged at a position between the subject eye and the visual target, the position being closer to the visual target than a concave mirror of the correction unit.

17. The subjective eye refracting power measurement apparatus according to claim 1, wherein the correction of the positional deviation is made by moving an optical member arranged at a position between the visual target and the subject eye, wherein the optical member for the correction is arranged at a position between the concave mirror and the correction optical system.

18. The subjective eye refracting power measurement apparatus according to claim 1, wherein the correction optical system comprises a pair of correction optical systems for each left subject eye and right subject eye, respectively, the pair of correction optical systems sharing the concave mirror.

19. The subjective eye refracting power measurement apparatus according to claim 9,
wherein when the direction of the subject eye is changed from the horizontal direction to the direction tilted downward from the horizontal direction, the incident angle of the flux of light of the visual target to the subject eye is changed, and
wherein the optical member for switching the light path is arranged between a second concave mirror and the correction optical system.

20. The subjective eye refracting power measurement apparatus according to claim 9, wherein the correction optical system comprises an optical unit arranged at a position between the subject eye and the visual target, the position being closer to the visual target than a concave mirror of the correction unit.

* * * * *